United States Patent
Seth et al.

(10) Patent No.: US 12,239,665 B2
(45) Date of Patent: *Mar. 4, 2025

(54) METHODS OF TREATING CANCER USING NK CELLS

(71) Applicant: Honed Life Sciences, LLC, Irvine, CA (US)

(72) Inventors: Avinash Seth, San Dimas, CA (US); Nikko Lowe, City of Industry, CA (US); Robert D. Fish, Irvine, CA (US)

(73) Assignee: HONED LIFE SCIENCES, LLC, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/077,938

(22) Filed: Dec. 8, 2022

(65) Prior Publication Data

US 2023/0109431 A1 Apr. 6, 2023

Related U.S. Application Data

(62) Division of application No. 16/831,244, filed on Mar. 26, 2020, now Pat. No. 11,547,726.

(51) Int. Cl.
| | |
|---|---|
| *A61K 35/17* | (2015.01) |
| *A61K 35/545* | (2015.01) |
| *A61P 35/00* | (2006.01) |
| *C12N 5/074* | (2010.01) |
| *C12N 5/0775* | (2010.01) |
| *C12N 5/0783* | (2010.01) |
| *C12N 5/0789* | (2010.01) |

(52) U.S. Cl.
CPC ............ *A61K 35/17* (2013.01); *A61K 35/545* (2013.01); *A61P 35/00* (2018.01); *C12N 5/0646* (2013.01); *C12N 5/0647* (2013.01); *C12N 5/0667* (2013.01); *C12N 5/0696* (2013.01)

(58) Field of Classification Search
CPC ....... A61K 35/17; A61K 35/545; A61P 35/00; C12N 5/0646; C12N 5/0647; C12N 5/0667; C12N 5/0696
See application file for complete search history.

(56) References Cited

U.S. PATENT DOCUMENTS

| | | |
|---|---|---|
| 6,849,452 B1 | 2/2005 | Zitvogel et al. |
| 8,372,642 B2 | 2/2013 | Rajesh et al. |
| 9,260,696 B2 | 2/2016 | Kaufman et al. |
| 2012/0148553 A1 | 6/2012 | Hariri et al. |
| 2013/0287751 A1 | 10/2013 | Kaufman et al. |
| 2016/0361360 A1 | 12/2016 | Chang et al. |
| 2018/0002438 A1* | 1/2018 | Kaufman ............ A61K 39/4631 |

FOREIGN PATENT DOCUMENTS

| | | |
|---|---|---|
| WO | 2001068896 A1 | 9/2001 |
| WO | 2012128622 | 9/2012 |
| WO | 2021015615 | 1/2021 |

OTHER PUBLICATIONS

Zhu et al. "Human pluripotent stem cells to produce cell-based cancer immunotherapy." Stem Cells. Feb. 2018; 36(2): 134-145. (Year: 2018).*
Marofi et al. "Renaissance of armored immune effector cells, CAR-NK cells, brings the higher hope for successful cancer therapy." Stem Cell Research & Therapy vol. 12, Article No. 200 (2021) (Year: 2021).*
Lian et al. "Challenges and Recent Advances in NK Cell-Targeted Immunotherapies in Solid Tumors." Int J Mol Sci. Dec. 23, 2021;23(1):164. (Year: 2021).*
Navin et al. "Design and Implementation of NK Cell-Based Immunotherapy to Overcome the Solid Tumor Microenvironment." Cancers 2020, 12(12), 3871 (Year: 2021).*
Lee et al. "Modeling Familial Cancer with Induced Pluripotent Stem Cells." Cell. Apr. 9, 2015; 161(2): 240-254. (Year: 2015).*
Li et al. "Human iPSC-Derived Natural Killer Cells Engineered with Chimeric Antigen Receptors Enhance Anti-tumor Activity." Cell Stem Cell.Aug. 2, 2018;23(2):181-192.e5 (Year: 2018).*
Cao et al. "Use of chimeric antigen receptor NK-92 cells to target mesothelin in ovarian cancer." Biochem Biophys Res Commun. Mar. 26, 2020;524(1):96-102. Epub Jan. 22, 2020. (Year: 2020).*
Alsberg, Eben et al., "Environmental Cues to Guide Stem Cell Fate Decision for Tissue Engineering Applications", Expert Opinion on Biological Therapy, Oct. 2006, pp. 847-866.
Shoae-Hassani, Alireza et al., "Natural Killer Cells from the Subcutaneous Adipose Tissue Underexpress the NKp30 and NKp44 in Obese Persons and Are Less Active against Major Histocompatibility Complex Class I Non-Expressing Neoplastic Cells", Frontiers in Immunology, Nov. 2017, vol. 8, Article 1486, pp. 1-9.
Li, Ye et al., "Human iPSC-Derived Natural Killer Cells Engineered with Chimeric Antigen Receptors Enhance Antitumor Activity", Cell Press, Cell Stem Cell 23, Aug. 2, 2018, pp. 181-192.
Levi, Benjamin et al., "In Vivo Directed Differentiation of Pluripotent Stem Cells for Skeletal Regeneration", PNAS, Dec. 11, 2012, vol. 109, No. 50, pp. 20379-20384.
Williams, Ian M. et al., "Generation of Endothelial Cells From Human Pluripotent Stem Cells", Arterioscler Thromb Vasc Biol., Jul. 2019, vol. 39, pp. 1317-1329.
Ning, NPL-01, Conversion of Adipose-Derived Stem cell.
Knorr, NPL-02, Pluripotent Stem cell-derived natural killer cells for cancer therapy.
Woll, NPL-03, Human embryonic stem cells differentiate.

(Continued)

*Primary Examiner* — Titilayo Moloye
(74) *Attorney, Agent, or Firm* — Fish IP Law, LLP

(57) ABSTRACT

Methods for generating clinically safe NK cells derived from non-fully differentiated stem cells and their use in treating cancer are provided. The non-fully differentiated stem cells are co-cultured with endogenous NK cells isolated from adipocyte-containing tissue to generate a high percentage of clinically safe NK cells, where anti-tumor activity of the clinically safe NK cells in vitro is similar to that of endogenous NK cells. Optimized Production of the clinically safe autologous NK cells from stem cells provides platform for treating cancer patients by applying an effective adoptive immunotherapy ranging from the early to terminal stages.

7 Claims, 1 Drawing Sheet

(56) References Cited

OTHER PUBLICATIONS

Chu, et al., "Co-culture of induced pluripotent stem cells with cardiomyocytes is sufficient to promote their differentiation into cardiomyocytes," PLOS ONE, Apr. 3, 2020, vol. 15, Issue 4, e0230966.15 pages.
Seet, et al. "Generation of mature T cells from human hematopoietic stem/progenitor cells in artificial thymic organoids," HHS Public Access, Nat Methods. May 2017 ; 14(5): 521-530. 25 pages.
Extended European Search Report for International Patent Application No. PCT/US2021/023454, dated Oct. 26, 2023, 10 pages.
Hiroyuki Matsubara, Induction of human pluripotent stem cell-derived natural killer cells for immunotherapy under chemically defined conditions, Biochemical and Biophysical Research Communications, dated Apr. 2, 2019, 8 pages, vol. 515.
Ning Hongxiu, Conversion of Adipose-Derived Stem Cells into Natural Killer-like Cells with Anti-Tumor Activities in Nude Mice, PLOS ONE, dated Aug. 2014, 11 pages, vol. 9.
Petter S. Woll, Human embryonic stem cells differentiate into a homogeneous population of natural killer cells with potent in vivo antitumor activity, Blood, dated Jun. 11, 2009, 8 pages, vol. 113.
David A. Knorr, Pluripotent stem cell-derived natural killer cells for cancer therapy, Traditional Research, dated Sep. 2010, 8 pages.
Fernanda C. Paccola Mesquita, Lamin as a Potent Substrate for Large-Scale Expansion of Human Induced Pluripotent Stem Cells in a Closed Cell Expansion System, Stem Cells International, dated Jan. 22, 2019, 10 pages, vol. 2019.

\* cited by examiner

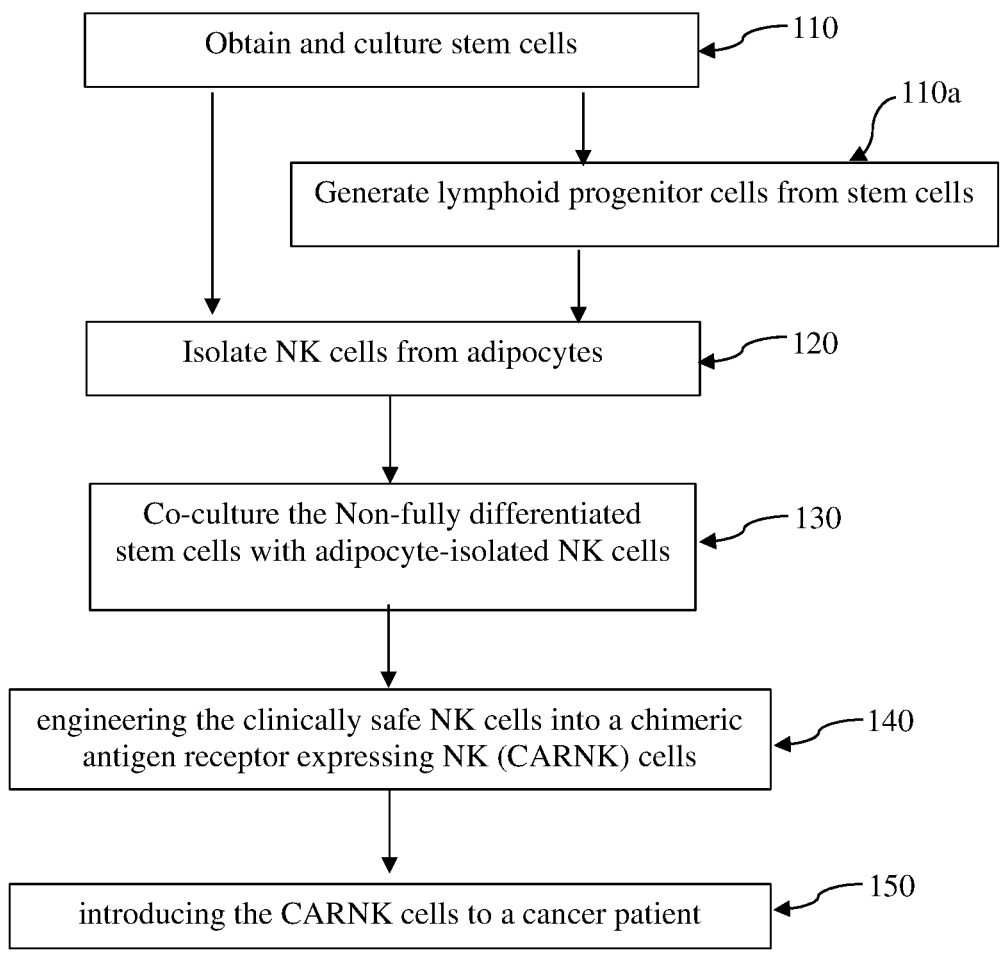

METHODS OF TREATING CANCER USING NK CELLS

This application is a divisional application of U.S. patent application Ser. No. 16/831,244 filed on Mar. 26, 2020. These and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

FIELD OF THE INVENTION

The field of the invention relates to compositions and methods for treating cancer.

BACKGROUND

The following description includes information that may be useful in understanding the present invention. It is not an admission that any of the information provided herein is prior art or relevant to the presently claimed invention, or that any publication specifically or implicitly referenced is prior art.

The American Cancer Society reports that more than 1.7 million new cancer cases will be diagnosed for 2019, and about 0.6 million Americans will have died of cancer in 2019. The funding for cancer research in America was more than 4 billion dollars in 2017 through the National Cancer Institute, and researchers are making endless efforts to develop effective cancer treatments.

Immunotherapy is a very exciting approach to developing anti-tumor treatments. As a part of its normal function, the immune system detects and destroys abnormal cancer cells, and immunotherapy helps the immune system to better act against cancer. One of these therapies is T-cell transfer therapy, which is a treatment that increases the natural ability of the patient's T cell to fight cancer. In this treatment, T cells are collected from a patient and engineered, such that engineered T cells are capable of detecting and binding to a specific antigen on the surface of cancer cells through the expression of an antigen-binding receptor on the surface of T cells. The engineered T cells are given back to the patient usually via a needle in the patient's vein(s). This therapy is called CAR (chimeric antigen receptor)-T cell therapy. CART cells can detect and bind cancer cells effectively and efficiently. As a result, CART cells can destroy cancer cells significantly more than the original T cells, and the anti-tumor activity of CART cells has been proven by many clinical trials.

Researchers have also experimented with generation of CARNK cells. There are some advantages of using NK cells rather than using T cells. First, unlike CART cells, CARNK cells retain an intrinsic capacity to detect and target cancer cells through their native receptors, so that it is less likely that cancer cells can escape from CAR cells by downregulating the CAR target antigen expression. Second, it is less likely that patients will suffer from cytokine release syndrome because CARNK cells do not undergo clonal expansion within days to weeks. Thus, the level of cytokines released from CARNK is maintained within the normal range. On the other hand, CART cells undergo clonal expansion, such that cytokine released from CART cells can reach a high level, and this high level of cytokines may cause increased inflammation throughout a patient body. This can result in organ failure or even death. Consequently, researchers have started to utilize NK cells to develop an effective anti-cancer treatment.

Because primary NK cells are difficult to isolate and purify, researchers have developed a protocol to generate NK cells using stem cells. These include induced pluripotent stem cells (iPSCs). An advantage of using iPSCs is that there is no immune rejection response from the patient. The iPSCs derived NK cells can be released back to an individual without concern for immune rejection because the iPSCs are obtained from the same individual. Additionally, there are already established protocols to differentiate iPSCs to NK cells, for example, shown in U.S. Pat. No. 9,260,696.

All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

However, there is at least one significant disadvantage using iPSCs. It is well known that undifferentiated iPSCs have intrinsically tumorigenic properties. On the other hand, differentiated cells derived from iPSCs lose tumorigenicity ("*The tumourigenicity of iPSCs and their differentiated derivates*", *J. Cell. Mol. Med.* Vol 17, No 6, P 782-791, 2013). When iPSC derived NK cells contaminated with undifferentiated iPSCs are introduced to a patient, the undifferentiated iPSC may differentiate into cancer cells in a body of the patient. Therefore, iPSC derived NK cells must be completely separated from undifferentiated iPSCs. Because the NK cells must be completely separated from undifferentiated iPSCs, a large amount of the NK cells are lost during separation of iPSCs from NK cells during the cell sorting process.

One way to reduce wasting large numbers of the generated NK cells is to increase the rate of the differentiation into NK cells. U.S. Pat. No. 9,260,696 teaches that, typically, only about half of stem cells (iPSCs and embryonic stem cells) are differentiated into NK cells in the presence of inactivated antigen presenting cells.

Qu el al. have used adipose-derived stem cells (ADSCs) that are differentiated into NK cells "*conversion of adipose-derived stem cells into Natural Killer-like cells with anti-tumor activities in nude mice, PLos ONE*, Vol 4, e106246, 2014". The efficiency of the ADSC differentiation to NK cells is not literally described, but in vitro results indicate that the efficiency is at least 90%.

There are two known ways to generate ADSC-derived NK cells. One is to use sphere clusters and the other way is to express E4BP (NK cell-specific transcription factor) in ADSCs. In vitro anti-tumor activity of NK cells developed from sphere clusters shows about 60% of the activity obtained from endogenous NK cells. On the other hand, in vitro anti-tumor activity of NK cells expressing E4BP is similar to the activity obtained from endogenous NK cells. This, in vitro anti-tumor activity of the NK cells expressed with E4BP is greater than the NK cell derived from sphere clusters. However, E4BP3 is expressed in ADSCs through lentivirus transduction of E4BP3 to ADSCs. There is a significant concern using such lentivirus exposed cells to treat cancer patients.

Thus, there is still a need for efficiently generating clinically safe NK cells from stem cells, having at least similar in vitro anti-tumor activity to the endogenous NK cells.

SUMMARY OF THE INVENTION

The inventive subject matter provides compositions and methods that provide a high percentage of stem cells that differentiate into clinically safe NK cells, having at least similar (e.g. 60%, 70%, 80%, 90%, 95%, or more than 95%) of the anti-tumor activity of endogenous NK cells in vitro.

The stem cells can include human induced pluripotent stem cells (iPSCs), adipocyte derived stem cells (ADSCs), embryonic stem cells, and hematopoietic stem cells.

The stem cells are used to create non-fully differentiated stem cells or undifferentiated NK precursor cells (These can be obtained by inducing the stem cells to form CD34+ hematopoietic precursor cells)

In some embodiments, NK cells can be isolated from a cluster of adipocytes. In other embodiments, NK cells are further purified from the Stromal Vascular Fraction of ADSCs. Co-culturing non fully differentiated stem cells derived from stem cells with the adipocyte-isolated NK cells provides a high efficiency of differentiation of stem cells into NK cells (e.g. greater than 50%, 60%, 70%, 80%, 90%, or 95%). In some embodiments, stem cells can be derived from the skin sample of individual and NK cells are derived from ADSCs of the same individual. In other embodiments, ADSCs can be isolated from such a cluster of adipocytes.

In some embodiments, at least 60% of the non-fully differentiated stem cells are differentiated into clinically safe NK cells as a result of co-culturing with the adipocyte NK cell. In preferred embodiments, at least 75% of the non-fully differentiated stem cells are differentiated into clinically safe NK cells. In most preferred embodiments, at least 90% of the non-fully differentiated stem cells are differentiated into clinically safe NK cells as a result of co-culturing with the adipocyte NK cell.

In some embodiments, in vitro anti-tumor activity of stem cell derived clinically safe NK cells is about 60% of the activity obtained from endogenous NK cells. In preferred embodiments, the anti-tumor activity of stem cell derived clinically safe NK cells is about 70% of the activity obtained from endogenous NK cells. In most preferred embodiments, the anti-tumor activity of stem cell derived clinically safe NK cells is about 90% of the activity obtained from endogenous NK cells.

In some embodiments, the co-culture does not include cytokines and/or growth factors.

The inventive subject matter also describes generating stem cell derived clinically safe NK cells, including steps of 1) isolating NK cells from a cluster of adipocytes, 2) expanding stem cells, 3) inducing stem cells to form non-fully differentiated stem cells 4) co-culturing the non-fully differentiated stem cells with the NK cell, 5) inducing differentiation of the non-fully differentiated stem cells into NK cells as a result of co-culturing. The co-culturing provides a high efficiency of differentiation of stem cells into NK cells having similar anti-tumor activity to endogenous NK cells. In some embodiments, a step of isolating stem cell derived NK cells from a mixture of stem cell derived NK cells and NK cells isolated from adipocytes is included.

The inventive subject matter further includes a method of treating a cancer patient using clinically safe NK cells derived from stem cells, comprising the steps described in the method above, and further including 1) engineering a stem cell derived clinically safe NK cell into a chimeric antigen receptor expressing NK (CARNK) cell, and 2) introducing the CARNK cell to a cancer patient.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Various objects, features, aspects and advantages of the inventive subject matter will become more apparent from the following detailed description of preferred embodiments, along with the accompanying drawing FIGURES in which like numerals represent like components.

BRIEF DESCRIPTION OF THE DRAWINGS

FIG. 1 is a schematic depiction of a method according to the inventive subject matter.

DETAILED DESCRIPTION

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

The recitation of ranges of values herein is merely intended to serve as a shorthand method of referring individually to each separate value falling within the range.

Unless otherwise indicated herein, each individual value is incorporated into the specification as if it were individually recited herein.

Unless the context dictates the contrary, all ranges set forth herein should be interpreted as being inclusive of their endpoints, and open-ended ranges should be interpreted to include only commercially practical values. Similarly, all lists of values should be considered as inclusive of intermediate values unless the context indicates the contrary.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

The current application provides compositions and methods in which a higher percentage of stem cells are differentiated into NK cells.

Definitions

The term "stem cell" refers to special cells that have the ability to develop into many different cell types, including muscle cells, brain cells, and red and white blood cells. Stem cell-based therapies can be used to treat a variety of ailments including cancer, and many clinical trials based on stem cell therapies are on-going. Stem cells include embryonic stem cells, adult stem cells including mesenchymal stem cells, hematopoietic stem cell, and adipocyte derived stem cells (ADSC), and induced pluripotent stem cells (iPSCs) including ADSC-derived iPSCs, and ectoderm/mesoderm/endoderm-derived stem cells.

The term "induced pluripotent stem cells" refers to a type of pluripotent stem cells that can be generated directly from somatic cells. One advantage of using iPSCs is that there is no concern for immune rejection. Indeed, iPSC developed from somatic cells obtained from an individual can be applied to the same individual.

The term "lymphoid progenitor cells" or "undifferentiated NK cells" refers to CD34+ hematopoietic precursor cells that are derived from stem cells.

The term "non-fully differentiated stem (NFDS) cells" refers to stem cells and lymphoid progenitor cells.

The term "patient-specific adipocytes/NK cells" refers to the adipocyte/NK cells derived/isolated from the individual.

The term "clinically safe NK cells" refers to NK cells that do not provide a clinically significant risk of introducing medical concerns that are endogenously and/or intrinsically originated from the NK cells. Thus, exogenous effects of the NK cells, for example, immune rejection and medical concerns as a result of environmental effects, are excluded.

The term "endogenous NK cells" refers to the NK cells that naturally develop into NK cells in the individual, including NK cells purified and isolated from the Stromal Vascular Fraction of ADSCs. NK cells in the blood stream are one example.

The term "in vivo" refers to a medical test, experiment, or procedure that is done on/in a living organism, such as a laboratory animal or human.

The term "in vitro" refers to a medial study or experiment, which is done in the laboratory within the confines of a test tube/laboratory dish.

Stem Cells

In some embodiments, adipocyte derived stem cells (ADSCs) can be used as stem cells (FIG. 1, 110). As described below, adipocyte residing NK cells can be isolated from human adipocyte-containing tissue obtained from a patient's subcutaneous fat. In some embodiments the same adipocyte-containing tissue can be used to isolate ADSCs. Taking fat tissue from a patient and isolating ADSCs from the tissue is relatively straightforward compared to isolating stem cells from bone marrow. For example, such tissue can be obtained by excision from a readily accessible subcutaneous site, or, alternatively, obtained by a liposuction procedure. It should be appreciated that a large number of ADSCs per volume of tissue, a high rate of proliferation, and anti-apoptotic function in ADSCs relative to other stem cells have been demonstrated in various preclinical studies. Accordingly, the size of an adipose tissue sample for such a process can be relatively small (e.g. from about 1 cm$^3$ to about 1,0000 cm$^3$). In addition, as described above, it is already known that ADSCs are capable of differentiating into NK cells. Alternatively, suitable stem cells can be obtained from any patient ectodermal, mesodermal, or endodermal tissue.

In some embodiments, iPSCs can be used as stem cells. As noted above, one advantage of the use of iPSCs is the minimal to no risk of immune rejection, as the iPSCs will be used to treat the individual that they are obtained from. Such iPSCs can be generated from any suitable ectodermal, mesodermal, or endodermal tissue. For example, fibroblasts isolated from a patient's skin can be used to generate suitable iPSCs.

It should be appreciated that the use of embryonic stem cells usually creates immune rejection because embryonic stem cells are not a patient-specific cells. Accordingly, use of iPSCs provides a significant technical advantage, especially for immunotherapy. The lack of rejection permits maintenance of immune function to be maintained to at least to a normal level.

In a preferred embodiment, iPSCs derived from ADSCs can be used. A method of generating such iPSC is taught in "*Induced Pluripotent Stem Cells Generated from Human Adipose-Derived Stem Cells Using a Non-Viral Polycistronic Plasmid in Feeder-Free Conditions, PLoS ONE, 7(10), 2012*".

iPSCs Derived from Patient Specific Fibroblasts

In one example of a method of the inventive concept a virus-free polycistronic plasmid method was applied to generate iPSCs from patient specific fibroblasts s. Taking a virus free polycistronic plasmid, pIRES2-EGFP plasmid, as a basic backbone, four "Yamanaka" genes (human OCT4, Sox2, Klf4, and c-Myc TF genes) were inserted into the vector in oskm order within a single open reading frame. The pIRES2-EGFP plasmid vector can be transfected into somatic cells without the need for viral packaging. The iPSCs derived from ADSCs are detected in a feeder cell-free environment with ectopic expression of the "Yamanaka" four factors. The iPSCs were further confirmed by the identification of major ES cell markers such as TRA-1-60, OCT4, Nanog and SSEA4 after 28 days of culturing. The iPSCs formed teratomas that differentiated into all three germ layers (i.e. endoderm, ectoderm, and mesoderm), indicating that iPSCs derived from ADSCs were successfully generated.

iPSCs can be expanded, for example, using culture in laminin 521 coated vessels, typically doubling in population within 7 days of culturing. Such expanded iPSCs can be banked for later use as described in "*Laminin as a potent substrate for large-scale expansion of human induced*

*pluripotent stem cells in a closed cell expansion system, Stem cells international,* 2019".

Some NK cells are found circulating in blood while others are tissue residents. In the current subject matter, NK cells residing in adipocytes can be obtained by isolation of NK cells from a patient-specific adipocyte-containing tissue (*"retained NK cell phenotype and functionality in non-alcoholic fatty liver disease, Frontiers in Immunology*, Vol 10, 1255, 2019"). The tissue is mechanically dissociated (e.g. by enzymatic digestion in collagenase II at 37° C.) and filtered through a 100 µm filter, and stained for the presence of NK cell-specific markers (for example, CD56, CD3-, etc.). Cells with NK cell markers are separated from other cell types, for example by flow cytometry.

Non-Fully Differentiated Stem Cells Co-Cultured with Adipocyte-Isolated NK Cells It should be appreciated that stem cells utilized in methods of the inventive concept can be totipotent or pluripotent (e,g, partially differentiated but not committed to maturing into a single cell type). Within the context of this application the term "non-fully differentiated stem cells" is considered inclusive of totipotent, pluripotent, multipotent, and oligopotent stem cells. Non-fully differentiated stem cells including stem cells and lymphoid progenitor cells (FIG. 1, 110*a*) can be cultured in DMEM-containing plastic culture dishes. The attached cells are allowed to reach 80% confluence. The isolated NK cells from adipocyte-containing (FIG. 1, 120) can be applied directly onto Non-fully differentiated stem cells in the culture dish, or they can be applied to a barrier (such as a divider or filter) that physically separates the stem cells from isolated NK cells (FIG. 1, 130). In the presence of such a barrier the Non-fully differentiated stem cells can, for example, be cultured on the surface of a bottom dish and NK cells isolated from adipocyte-containing tissue presented on a top culture dish. In such embodiments, molecules released from the NK cells can pass through the barrier and reach to the Non-fully differentiated stem cells. In some embodiments, cancer cells can be applied on the top dish and/or surface of the barrier to activate NK cells isolated from adipocyte-containing tissue.

The ratio of lymphoid progenitor cell to a NK cell isolated from adipocyte-containing tissue can range from 1:1 to 10,000:1. In some embodiments, the ratio is 1:1 to 1,000:1. In more preferred embodiments, the ratio is 1:1 to 1:10,000. Such co-culturing of these cells can be maintained for from 8 hours to 2 months, typically at 37° C. and with 5% $CO_2$.

NK cells isolated from adipocyte-containing tissue can be healthy (with or without activation), or damaged NK cells. In some embodiments, as described above, NK cells can be activated by co-culturing with cancer cells in the presence of a barrier between non-fully differentiated stem cells and NK cells with cancer cells. In some embodiments, NK cells are induced (activated) by introducing cytokines and/or growth factors (such as IL-2, IL-3, IL-6, IL-7, IL-15, IL-18, IFN-γ, and/or TNF-α). In some embodiments, damaged NK cells, for example, having lower cytotoxicity, can be used for co-culturing with stem cells.

The duration of such co-culturing can range from overnight to 10 weeks. In preferred embodiments, the duration is 3 days to 8 weeks. In more preferred embodiments, the duration is 1 week to 6 weeks. In the most preferred embodiments, the duration is 1 week to 4 weeks.

In some embodiments cell culture media used in such methods can include cytokines and/or growth factors. In other embodiments such cell culture media can exclude cytokines and/or growth factors. Suitable cytokines and/or growth factors include IL-2, IL-3, IL-6, IL-7, IL-15, IL-18, stem cell factor, endothelial growth factor, granulocyte-macrophage colony-stimulating factor, IFN-γ, and/or TNF-α.

Stem cells of the inventive concept can differentiate into various NK cells lines, including NK3.3, KHYG-1, NKL, NKYS, and NKT. The markers for NK3.3 lines include CD2, CD11a, CD38, CD45, CD16, and CD56. The markers for KHYG-1 lines include CD2, CD3ε, CD7, CD8αα, CD33, CD56, CD122, and CD132. The markers for NKL lines include CD2, CD3ε, CD7, CD8αα, CD33, CD56, CD122, and CD132. The markers for NKT lines include CD56, CD3. The markers for NKYS lines include CD2, CDS, CD7, and CD56.

Since all NK cell lines express CD56, and CD56 is specific to NK cells, in preferred embodiments cultured cells can be stained with CD 56 and separated by cell sorting in a flow cytometer to separate NK cells (including both stem cell derived NK cells and NK cells isolated from adipocyte-containing tissue) from undifferentiated stem cells.

Evaluation of Anti-Tumor Activity In Vitro

Cancer cells, for example, PC3 (human prostate cancer cell line, B Cell Lymphomas, HL-60 acute myeloid leukemia cell lines, U266 multiple myeloma cell lines, U87 glioblastoma multiforme cell lines, A549 non-small cell lung cancer cell lines, Saos-2 human osteosarcoma cancer cell lines, A673 Ewing sarcoma cell line) and non-cancer cells (for example, epithelial cells isolated from an individual) can be fluorescently labeled using, for example, an activated fluorescent dye such as carboxyfluorescein diacetate succinimidyl ester (CFSE). The cancer and/or non-cancer cells can be mixed with stem cell derived NK cells or NK cells isolated from adipocyte-containing tissue or blood at various ratios. The ratio of a cancer cells (and/or non-cancer cells) to NK cells can range from 1:1, 1:5, 1:10, 1:20: 1:50, and/or 1:100. After overnight incubation at 37° C. and 5% $CO_2$, cell culture can be stained with a dead cell marker (for example, propidium iodide or PI) and then analyzed by flow cytometry. The percentage of the dead cancer and/or non-cancer cells are calculated by comparing the number of PI stained cells to the number of CFSE stained cells.

Instead of using PI staining, cells can be observed microscopically to determine viability. A phase-contrast and a fluorescent image can be obtained from the same location in such a cell culture and superimposed. Intact and lysed CFSE-labeled can be counted randomly for selected images. The percentage of the dead cancer or non-cancer cells are calculated by comparing the number of stained lysed cells to the number of stained lysed and stained intact cells.

Evaluation of Anti-Tumor Activity In Vivo

Tumor cells, for example, U87 glioblastoma multiforme cell lines, PC3 (human prostate cancer), B Cell Lymphomas, HL-60 acute myeloid leukemia cell lines, U266 multiple myeloma cell lines, A549 non-small cell lung cancer cell lines, Saos-2 human osteosarcoma cancer cell lines, A673 Ewing sarcoma cell line) can be subcutaneously injected into a representative number (e.g. about fifteen) 2-month-old male nude mice at $1\times10^6$ cells/mouse. One week later, the mice are separated into 3 groups of approximately equal size. The first and second group are intravenously injected with $1\times10^7$ cells of either stem cell derived clinically safe NK cells or the endogenous NK cells specific to each individual mouse. The third group is a negative control. Tumor size can be measured (e.g. with an electronic caliper, by image analysis, etc.) at regular intervals for up to 8 weeks after PC3 injection. The tumor size can be calculated as length (mm)×width$^2$ (mm$^2$)×0.523.

Generated NK cells can be used for immunotherapy including CARNK therapy (FIG. 1, 140) against cancers and applied to a patient to treat their cancer (FIG. 1, 150). In addition, extracellular vesicles derived from such NK cells can be used to produce an anti-tumor effect. The stem cell derived clinical safe NK cells can be used to obtain such extracellular vesicles for application to cancer therapy in humans. Therefore, generated NK cells described in the current subject matter are versatile enough to develop various treatments against cancers.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refer to at least one of something selected from the group consisting of A, B, C . . . and N, the text should be interpreted as requiring only one element from the group, not A plus N, or B plus N, etc.

What is claimed is:

1. A method of generating a CAR expressing NK cells (CARNK cells), comprising;
   isolating endogenous NK cells from a cluster of adipocytes;
   culturing non-fully differentiated stem cells;
   inducing differentiation of non-fully differentiated stem cells into stem cell derived NK cells by co-culturing the cultured non-fully differentiated stem cells with the endogenous NK cells, wherein the non-fully differentiated stem cells and the endogenous NK cells are separated by a barrier when in culture; and
   modifying the stem cell derived NK cells and the endogenous NK cells to express chimeric antigen receptor (CAR) to generate CARNK cells.

2. The method of claim 1, wherein non-fully differentiated stem cells are selected from the group consisting of lymphoid progenitor stem cells, human induced pluripotent stem cells (iPSCs), adipocyte derived stem cells (ADSCs), embryonic stem cells, and hematopoietic stem cells.

3. The method of claim 2, wherein iPSCs are iPSCs derived from fibroblasts obtained from a cancer patient.

4. The method of claim 2, wherein non-fully differentiated stem cells or the cluster of adipocytes are originated from a cancer patient.

5. The method of claim 1, wherein at least 60% of non-fully differentiated stem cells are differentiated into stem cell derived NK cells as a result of co-culturing with the endogenous NK cell.

6. The method of claim 1, wherein at least 75% of non-fully differentiated stem cells are differentiated into stem cell derived NK cells as a result of co-culturing with endogenous NK cells.

7. The method of claim 1, wherein at least 90% of non-fully differentiated stem cells are differentiated into stem cell derived NK cells as a result of co-culturing with endogenous NK cells.

\* \* \* \* \*